US010407494B2

(12) United States Patent
Mitteness

(10) Patent No.: US 10,407,494 B2
(45) Date of Patent: Sep. 10, 2019

(54) IMMUNOGEN ADHERENCE AND METHOD OF MAKING AND USING SAME

(71) Applicant: Camas Incorporated, Le Center, MN (US)

(72) Inventor: Bradley M. Mitteness, Ghent, MN (US)

(73) Assignee: CAMAS INCORPORATED, Le Center, MN (US)

( * ) Notice: Subject to any disclaimer, the term of this patent is extended or adjusted under 35 U.S.C. 154(b) by 0 days.

(21) Appl. No.: 15/645,693

(22) Filed: Jul. 10, 2017

(65) Prior Publication Data

US 2017/0362308 A1 Dec. 21, 2017

Related U.S. Application Data

(62) Division of application No. 10/775,557, filed on Feb. 10, 2004, now Pat. No. 9,701,737.

(60) Provisional application No. 60/447,904, filed on Feb. 19, 2003.

(51) Int. Cl.

| | |
|---|---|
| ***C07K 16/12*** | (2006.01) |
| ***C07K 16/02*** | (2006.01) |
| ***C07K 16/24*** | (2006.01) |
| ***A61K 39/00*** | (2006.01) |

(52) U.S. Cl.

CPC .......... *C07K 16/1242* (2013.01); *C07K 16/02* (2013.01); *C07K 16/247* (2013.01); *A61K 2039/505* (2013.01)

(58) Field of Classification Search

CPC ........... A23J 1/08; C07K 16/02; C07K 16/06; C07K 16/12; A61K 39/00; A61K 35/54

USPC ..... 424/130.1, 157.1, 183.1, 186.1; 530/423, 530/853, 861

See application file for complete search history.

(56) References Cited

U.S. PATENT DOCUMENTS

| | | | | |
|---|---|---|---|---|
| 4,166,867 A | 9/1979 | Betz et al. | | |
| 4,748,018 A * | 5/1988 | Stolle | C07K 16/02 | 424/157.1 |
| 4,748,019 A | 5/1988 | Lysons | | |
| 5,080,895 A | 1/1992 | Tokoro | | |
| 5,196,193 A | 3/1993 | Carroll | | |
| 5,367,054 A | 11/1994 | Lee | | |
| 5,420,253 A * | 5/1995 | Emery | A23J 1/08 | 424/157.1 |
| 5,443,976 A | 8/1995 | Carroll | | |
| 5,556,744 A * | 9/1996 | Weiner | C07K 14/005 | 435/5 |
| 5,585,098 A | 12/1996 | Coleman | | |
| 5,753,268 A | 5/1998 | Stolle et al. | | |
| 6,068,862 A | 5/2000 | Ishihara et al. | | |
| 6,086,878 A | 7/2000 | Adalsteinsson et al. | | |
| 6,156,726 A | 12/2000 | Newcomb et al. | | |
| 6,337,070 B1 | 1/2002 | Okuno et al. | | |
| 2002/0012666 A1 | 1/2002 | Greenblatt et al. | | |
| 2002/0098181 A1* | 7/2002 | Nash | C07K 16/02 | 424/130.1 |
| 2002/0117552 A1 | 8/2002 | Traylor | | |
| 2004/0161427 A1 | 8/2004 | Nash et al. | | |
| 2007/0218114 A1 | 9/2007 | Duggan et al. | | |
| 2011/0033544 A1 | 2/2011 | Nagata et al. | | |
| 2011/0166328 A1 | 7/2011 | Nguyen | | |
| 2013/0183286 A1 | 7/2013 | Mitteness et al. | | |

FOREIGN PATENT DOCUMENTS

| | | | | |
|---|---|---|---|---|
| FR | 2810550 A1 | | 12/2001 | |
| JP | 62-175426 A | | 8/1987 | |
| WO | WO 1996/012802 | * | 5/1996 | C12N 15/09 |
| WO | WO 2000/027410 | * | 5/2000 | A61K 35/54 |
| WO | WO 2001054717 | * | 8/2001 | A61K 35/76 |
| WO | 2007068154 A1 | | 6/2007 | |

OTHER PUBLICATIONS

Adachi et al. (Experimental and Therapeutic Medicine. 2011; 2: 41-45).

Avadhanula et al., "Respiratory viruses augment the adhesion of bacterial pathogens to respiratory epithelium in a viral species and cell type-dependent manner." J. Viral., vol. 80, No. 4, pp. 1629-1636 (2006).

Beck et al. (Avian Diseases. 2003; 47: 1196-1199).

Cuceanu et al. (Roum Arch Microbial. Immunol. Jul.-Sep. 1991; 50 (3): 215-22, abstract only).

Ewert et al. (Infection and Immunity. Apr. 1979; 24 (1): 269-275).

(Continued)

*Primary Examiner* — Jana A Hines

(74) *Attorney, Agent, or Firm* — Westman, Champlin & Koehler, P.A.; Z. Peter Sawicki; Visala C. Goswitz

(57) ABSTRACT

A microbial adherence inhibitor in the form of fowl egg antibodies is disclosed, along with the method of making it and methods of using it. The inhibitor functions by substantially preventing the attachment of adherence of colony-forming immunogens in the respiratory tracts of host animals and humans. The inhibitor is made by inoculating female birds with the immunogen, harvesting the eggs which contain antibodies to the immunogen, and separating the yolk and albumin from the shells of the eggs. The yolk and albumin contents are administered to animals or human by distributing the contents directly or introducing the contents entrained in air.

15 Claims, No Drawings

(56) References Cited

OTHER PUBLICATIONS

Hament et al., "Enhanced adherence of *Stretococcus pneumoniae* to human epithelial cells infected with respirator syncytial virus." Pediatric Research, vol. 55, No. 6, pp. 972-978, 2004.

http://convert-to.com/725/quail-eggs-nutrition-details-units-conversion.html; pp. 3-6; accessed Jun. 23, 2016.

Lee et al. (Journal of Pharmaceutical Sciences. Jul. 2000; 89 (7): 850-866).

Nierynck et al. (Nature Medicine. Oct. 1999; 5 (10): 1157-1163).

Pauly et al. "IgY technology: extraction of chicken antibodies from egg yolk by polyethylene glycol (PEG) precipitation." Journal of visualized experiments: JoVE 51 (2011).

Ramos-Vara et al., Metritis, valvular endocarditis, and septicemia by actinobacillus equuli in a gilt in the United States, Vet. Pathol., vol. 45, pp. 495-499, 2008.

Snowder et al., Bovine respiratory disease in feedlot cattle: environmental, genetic and economic factors, American Socity of Animal Science, Vo. 84, pp. 1999-2008, 2006.

Smith, Dental caries vaccines: prospects and concerns, Critical Reviews in Oral Biology & Medicine, vol. 13, No. 4, pp. 335-349, 2002.

USDA Agriculture Research Service Nutritional Nutrient Database for Standard Reference Release 27; Basic Report 01123, Egg, whole, raw, fresh. Feb. 26, 2015.

Christopher-Henning, J., K. S. Faaberg, M.P. Murtaugh, E.A. Nelson, M.B. Roof, E. M. Vaughn, K.J. Yoon, and J.J. Finnerman, Porcine reproductive and respiratory syndrome (PRRS) diagnostics: Interpretation and limitations & Swine Health and Production; 10(5); 213-218, 2002.

Corbeil L B et al.: "Bovine IgG2a antibodies to haemophilius somnus and allotype expression." Canadian Journal of Veterinary Research, vol. 61, Jul. 1997 (Jul. 1997), pp. 207-213, Canada.

Examiner's Report Issued in Corresponding Brazilian Patent Application No. P10407612-5, dated Aug. 23, 2016.

Faber, R., N. Hartwig, D. Busby and R. BreDahl, The costs and predictive factors of bovine respiratory diseases in standardized steer tests, 1999 Beef Research Report, Iowa State University, 11 pages, A.S. Leaflet R1648, 1999.

Hatta, H, Tsuda, K., Akachi., S. et. al. Oral passive immunization effect of anti-human rotavirus IgY and its behavior against proteolytic enzymes. 1993. Bioscience, biotechnology, and biochemistry. 57(7): 1077-1081.

Japanese Laid-Open No. S62-215535.

Japanese Unexamined Patent Application Publication No. 2001-515050.

Jones G E et al.:"Protection of lambs against experimental pneumonic pasteurellosis by transfer of immune serum." Veterinary Microbiology, vol. 20, May 1989 (May 1989), pp. 59-71, Netherlands.

Kirkwood et al., (J. of Swine Health and Production. vol. 9(2):77-79).

Krause et al. An rRNA Approach for Assessing the Role of Obligate Amino-Acid-Fermenting Bacteria in Ruminal Amino Acid Deamination. Mar. 1996, Applied and Environ. Micro, vol. 62, No. 3, pp. 815-821.

Lin, C.B. A molecular approach to the differntials of atypical actinobacillus pleuropneumoniae field strains isolated in the United States, Am. Association Swine Vet: 209-213, 2002.

Lin, C.B. Intraspecies differentiation of mycoplasma hypopneumoniae field stains isolated in the United States, Am. Association Swine Vet: 225-235, 2001.

Lu Y S; Lai W C; Pakes S P; Nie L C: "A monoclonal antibody against a Pasteurella multocida outer membrane protein protects rabbits and mice against pasteurellosis." Infection and Immunity, vol. 59, No. 1, Jan. 1991 (Jan. 1991), pp. 172-180, US.

Miniats O P et al.: "Vaccination of gnotobiotic primary specific pathogen-free pigs against Haemophilus parasuis." Canadian Journal of Veterinary Research, vol. 55, Jan. 1991 (Jan. 1991), pp. 33-36, Canada.

Office Action, Brazilian Patent Application No. 0407612-5 "Immunogen Adherence Inhibitor for Respiratory Tract and Methods for Making and Using Same" dated Feb. 28, 2012.

Office Action,Canadian Patent Application No. 2516087, Antibodies Against Respiratory Ailment-Causing Pathogens, dated Nov. 21, 2011.

Otae, S., S. A. Dee, and C. Pijoon, Transmission of PRRSO: Recent research reports, Intronataral Piglets, 22(7): 37, 40-42, 2002.

Part 1: reference of swine health and management in the U.S. 2000, National Animal Health Monitoring System (NAHMS), Swine Survey 2000, USDA-APHIS, 2000.

Peralta, R.C., Yokoyama, H., Ikemori, Y., Et al. Passive immunisation against experimental salmonellosis in mice by orally administered hen egg-yolk antibodies specific for 14-kDa fimbriae of *Salmonella enteritidis*. 1994. J. Med. Microbiol. 41: 29-35.

Regula, G et al. Comparisons of serological testing and slaughter evaluation for assessing the effects of subclinical infection on growth in pigs. G AUMA 217(6): 888-895, 2000.

Rimler; R B: "Passive immune cross-protection in mice produced by rabbit antisera against different serotypes of Pasteurella multocida" Journal of Comparative Pathology, col. 114, No. 4, May 1996 (May 1996) pp. 347-360, XP005468735 London, GB.

Sheidt, A. Mycoplasma pneumonia, Proceedings of North Carolina Healthy Hogs Seminar, 2 pages, North Carlonia Swine Veterinary Sweep, 1993.

Shin, N.R., Choi, I.S., Kim, J.M., et al. Effective methods for the production of immunoglobulin Y using immunogens of Bordetella bronchiseptica, Pasteurella multocida and Actinobacillus pleuropneumoniae. 2002. J. Vet. Sci. 3(1): 47-57.

Smith et al., (Infection and Immunity. 2001 vol. 69(5): 3135-3142).

Straw, B.A. and L.K. Clark, Mycoplasma pneumonia of swine, Purdue University, Cooperative Extension Service, P1H-29, 5 pages.

Stovall, T.C., D.R. Gell, R.A. Smith, and R.L. Ball, Impact of bovine respiratory disease during the receiving period on feedlot performance and carcass Traits, 2000 Animal Science Peswich Report pp. 82-86, 2000.

Thacher, E. & B. Jonke, Which bag is it? SIV or M. Hyo? Focus on Swine Health & Performance, 5(3): 1-4, 2001.

Van Donkersgoed et al. (Can Vet J. vol. 36 Jul. 1995. pp. 425-429).

Veterinary Services, Info Sheet: treatment of Respiratory Disease in U.S. Feedlots, Oct. 2001, 4 pages #N 347-1001, USDA-APHIS, 2001.

Weltzin et al., (Clin Micro Rev. 1999. vol. 12(3): 383-393).

Yaerger, M. The impact of exposure dose on PRRSO induced reproductive disease in vaccinated and unvaccinated cows, Proceedings of Swine Disease conference for Swine Practitioners, Nov. 74-75, 1999.

Yokoyam et al. Passive Protective Effect of Chicken Egg Yolk Immunoglobulins Against Experimental Enterotoxigenic *E. coli*, Infection in Neonatal Piglets. Mar. 1992. Infect and Immun. vol. 60, No. 3, pp. 998-1007. See entire document.

Roy, S.K. et al. "Bioadhesive Polymeric Platforms for Transmucosal Drug Delivery Systems—a Review" Trop J Pharm Res, 9, pp. 91-104, Feb. 2010 (Feb. 2010).

Office Action issued for related Canadian patent application No. 2,798,151, dated Nov. 16, 2018.

* cited by examiner

IMMUNOGEN ADHERENCE AND METHOD OF MAKING AND USING SAME

CROSS REFERENCE TO RELATED APPLICATION

The present application is a divisional of and claims priority of U.S. patent application Ser. No. 10/775,557, filed Feb. 10, 2004, which is based on and claims the benefit of U.S. provisional patent application Ser. No. 60/447,904 filed Feb. 19, 2003.

FIELD OF THE INVENTION

This invention is direct to microbial adherence inhibitors, in the form of fowl egg antibodies, for substantially preventing the attachment or adherence of colony-forming illness-causing immunogens in respiratory disease complex by inhibiting the immunogen to adhere to the mucous membranes of animals including host food animals, high value nonfood animals, zoological animals, companion animals, laboratory animals or humans, to the method of producing such adherence inhibitors, and to the methods of using such inhibitors.

BACKGROUND OF THE INVENTION

A group of microorganisms form a very complex interaction in the respiratory tract of animals. These animals can be dairy cattle, feedlot cattle, swine, and birds such as chickens and turkeys to name a few. Although the organisms can vary from animal group to animal group, they are basically bacteria such as *Pasteurellae, Mannhiemae*, and *Haemophilus* groups, *Mycoplasma*, and viruses of the respiratory groups such as bovine respiratory syncytial virus (BRSV), bovine viral diarrhea (BVD), parainfluenza (PI-.sub.3), infectious bovine rhinotrocheitus (IBR), swine influenza, (H.sub.1N.sub.1,H.sub.3N.sub.2), fungi and parasites and combinations of the same. These organisms are consisted as opportunistic respiratory pathogens that may reside in the upper respiratory tract of healthy animals. *Pasteurella* and to a lesser extent *Haemophilus* and *Mycoplasma* species may cause bovine respiratory disease complex (BRDC) in cattle by the result of invasion of the lower respiratory tract after endogenous injections of the nasopharynx. In dairy or feedlot cattle, a variety of stressful situations such as shipment, weaning, viral infections, bad weather, change in weather, movement in feedlots, poor nutrition, and overcrowding can impair the competence of the immune system and the physical and immunological defenses of the animals. This allows greater numbers of microorganisms to make the journey from the nasopaharyngeal area to the lower respiratory tract to the interior of the lungs. This leads to the pneumonic respiratory disease complex, which includes the shipping fever complex in cattle. Transmission between animals is usually by airborne droplets or by food or water contamination. Once the microorganisms are established in the nasopharyngeal area, during inspiration the aerosols can result in downward carriage of the bacterial into the lower respiratory tract. This allows the organisms to attach to the bronchi and alveolar cells and to multiply causing pneumonia. Lung infections can lead to lesions with no clinical signs but lead to lower average daily gain. Animals can go off feed, become very ill rapidly and death can occur within hours. Morbidity can be very high and once one animal becomes ill the rest of the herd are easier to infect. This becomes a major concern for feedlots. Similar outbreaks occur in swine herds and flocks of birds such as chickens and turkeys. Current live vaccines have had limited success in protecting the animals against this complex. This may in part be due to the lack of immune protection in the nasopharyngal area. Although the group of respiratory viruses can weaken the animals and decease the immunological response of the host, it is the bacterial strains (usually *Mannhiema hemolytica* or *Pasteurella multocida*) that invade the lower respiratory tract leading to broncho-pneumonia (BRD) that lead to disease and death of the animal. In both shipping fever pneumonia and enzootic pneumonia in cattle, the final common denominator in both types of disease are the bacterial agents. Bovine respiratory disease (BRD) is the leading cause of disease related loss in feedlots today. Financial losses attributed to BRD include mortality, medication, veterinary, and labor costs for treatment. Average costs for one treatment average $8.80 per head. Heifers treated for BRD have lower morbidity scores by 37.9%. Animals that are never treated average $11.48 per head higher in net return. The average daily gains differ between treated and untreated animals. The net profit averages $57.48 lower per head for treated animals. BRD has been listed as causing 20.6% of all steer deaths in feedlots.

Porcine respiratory disease complex is a major and similar type of disease affecting up to 90% of all swineherds. *Mycoplasma hypopneumonia* is the primary pathogen commonly associated with the complex secondary pathogens such as *Pasteurella multocida* types A and D and can cause clinical signs of high fever or impaired growth. Combinations of these organisms can lead to both increase in severity and duration of pneumonia in swine. Porcine reproduction and respiratory syndrome (PRRS) can be another major cause of pneumonia in swine. This can lead to severe reproduction disease with only minimal dose of virulent PRRS stains. Common causation agents of Swine respiratory disease can include PRRS virus, swine influenza (H1N1, H3N2) and *Mycoplasma hypopneumoniae* along with *Haemophilus parasuis, Haemophilus suis, Haemophilus planopneumonia, Pasteurella* (*Mannhiema*) *haemolytica* and *Pasteurella multocida* (types A & D). Estimating the total economic impact on the health of these animals is difficult. Pneumonic lung lesions may cause poor respiratory health in herds and may affect up to 70 percent of the pigs in a herd. Combinations of vaccinations for viruses and medication for bacteria are needed to help control these problems—timing of vaccination is always important. Medication must be applied at the proper time to minimize costs and damage to the animals.

Organisms such as *Mycoplasma hypopneumoniae* can be a cause an important chronic respiratory disease called "swine enzootic pneumonia" (SEP). This organism alone can produce severe pneumonia in swine and remains a significant threat to the swine industry.

*Actinobacillus pleuropneumoniae* causes "porcine pleuropneumoniae", resulting in serious financial losses and death. Although vaccines have been developed, homologous protection has not been demonstrated. During the past years, 14 serotypes and 2 biotypes have been identified worldwide. Both growing and finishing pigs must be vaccinated to protect herds.

The primary effect of respiratory disease in swineherds is seen in reduced feed intake that leads to impaired growth. This leads to less uniformity in pigs, more mortality, less average daily gain, and less pigs per litter. Producers report that almost 14.4% of all herd placements develop respiratory disease. Costs increase for injecting vaccines and medication, and lower overall performance. Estimates have been made that reduced daily weight gain and antibiotics used to treat disease cost the Swine industry 467 million dollars annually. Over 39% of all deaths in grower-finisher pigs had been attributed to respiratory diseases in swine.

PRIOR ART

The production of avian egg antibody for the diagnosis or treatment of specific conditions has been known. The production of avian egg antibody for the inhibition of organisms, specifically the colonization of organisms, and the adherence and colonization of illness-causing immunogens in the respiratory tracts of animals is not suggested.

Representative prior art patents include the following:

Polson, U.S. Pat. No. 4,555,019

Stolle et al, U.S. Pat. No. 4,748,019

Tokoro, U.S. Pat. No. 5,080,895

Carroll, U.S. Pat. No. 5,196,193

Lee, U.S. Pat. No. 5,367,054

Coleman, U.S. Pat. No. 5,585,098

Stolle et al, U.S. Pat. No. 5,753,268

Raun, U.S. Pat. No. 3,794,732, discusses the uses of polyester antibiotics in ruminant rations to improve the utilization of feed in ruminant animals. This specifically addresses the use of antibiotics in ruminant animals as growth promotants.

Raun, U.S. Pat. No. 3,947,836, discusses the use of specific antibiotic compounds for ruminant feed utilization improvement when given orally to the animal. Specifically, the animal develops rumen function where more propionates in relation to acetates are produced thus improving feed utilization.

Ivy et al, U.S. Pat. No. 4,933,364, discusses an alternative process for promoting growth and feed efficiency of food producing mammals. They propose the use of zinc antibiotic that can be added in insoluble form to create a zinc antibiotic complex which enhances feed efficiency of food producing mammals. They reference two U.S. Pat. Nos. 3,501,568 and 3,794,732, that cover monensin in great detail.

Other references on the use of additives such as monensin have mentioned the need for wise application of these materials because they can be toxic to some animals, such as horses. These antibiotics, which are not approved for use in dairy cows, must be administered carefully. In addition, feed intake is initially reduced as monensin cannot be added to molasses based supplements which are classic additives to cattle feeds. (Pate, F., “Ionophores Do Not Appear To Work In Molasses Supplements”, ONA Reports, November, 1966, 2 pages, Florida Cattleman and Livestock Journal; Lona, R. P. et al, J. Anim. Sci. 75(1): 2571-2579, 1979).

Polson, U.S. Pat. No. 4,550,019, is directed to the manufacture and use of fowl egg yolk antibodies for making immunological preparations for the passive immunizations of animals, including humans, as immuno reagents for immunosorbitive processes and in particular for quantitative analytical tests, especially micro assays for diagnostic, pathological, forensic, and pharmacokinectic investigations.

Stolle et al, U.S. Pat. No. 4,748,018, is directed to a method of passive immunization of mammals using avian egg yolk antibody against any of a variety of antigens using various methods of administration under various conditions and using various compositions incorporating the antibody, after first developing in the mammal a tolerance for the antibody.

Tokoro, U.S. Pat. No. 5,080,895, is directed to a specific antibody containing substance from eggs and method of production and use thereof for the treatment of infectious or other diseases, and as additives in food for livestock and poultry, cosmetics, and medicines, and in the field of serodiagnosis. Although not explicitly stated, it is apparent that the use of the egg antibody in feeds is to provide an easy means of oral administration of the antibody for the treatment of intestinal infections in livestock or poultry.

Carroll, U.S. Pat. No. 5,196,193, and divisional U.S. Pat. No. 5,443,976, are directed to anti-venom compositions containing horse antibody or avian egg yolk antibody for neutralizing snake, spider, scorpion or jelly fish venom.

Lee, U.S. Pat. No. 5,367,054, is directed to methods for large scale purification of egg immunoglobulins to lower somatic cell count in the milk of lactating ruminants.

Stolle et al, U.S. Pat. No. 5,753,268, is directed to an anti-cholesterolemic egg vaccine and method for production and use as a dietary supplement for the treatment of vascular disorders in humans and other animals.

SUMMARY OF THE INVENTION

Broadly stated, this invention is directed to a method for the production of a microbial adherence inhibitor for administration to animals, such as host food animals, high value nonfood animals, zoological animals, companion animals, or humans to inhibit or substantially prevent the adherence of colony-forming immunogens in the respiratory tracts by first inoculating female birds, in or about to reach their egg laying age, with the particular target immunogen. Then, after a period of time sufficient to permit the production in the bird of antibody to the targeted immunogen, the eggs laid by the birds are harvested. The yolk and albumin antibody-containing contents of the eggs are separated from the shells. The antibody-containing contents of the eggs may be used directly, placed on an extender, or mixed with carrier material. The antibody can be incorporated into a liquid, mixed into a lick tub, sprayed or squirted into the environment containing the animals. The egg antibody adherence inhibiting material maybe stored or shipped for use as needed.

The egg contents incorporating the antibody specific to the targeted immunogens are administered to the animals or humans by distributing the antibody material directly or introducing antibody material entrained in air. The material can be introduced into the nasal pharyngeal area of the animal by direct injection with a syringe or sprayed. The material can be administered with a squirt gun directly or intranasal inoculation. Aerosol mixtures can be made and administered as a mist over the heads and nostrils of the animals. Another alternative is to mix the material with a carrier and administer as “top dressing” on feed. Special needs can be met by adding the material to water and letting the animals or humans drink the solution. The active material can be added to bulk licks or feed baskets for delivery. Gel-like mixtures can be made using common animal feed mixtures and pouring into “lick tubs” (feed additive bulk tubs). Other delivery systems can be adapted for delivery of the active material to the respiratory tract.

DESCRIPTION OF THE PREFERRED EMBODIMENTS

The present invention is predicated on a method of inhibiting the ability of colony forming microorganisms, such as *Pasteurella* (*Mannhiema*) *haemolytica, P. multocida*, and *Haemophilus somnus*, Swine influenza, *Mycoplasma bovis* or *M. hypopneumoniae* from adhering to the mucous membranes and bronchi and alveolar cells of the respiratory tracts of animals thereby preventing colonization of the microorganisms. The failure of the microorganisms to colonize maintains the immunological defenses of the animals when subjected to stress inducing environments. The result is that the animals have less pneumonic respiratory diseases including shipping fever which cause high mortality of infected animals.

All mammals and birds provide similar types of protection which allow for an immediate immune response in their very young offspring until they too acquire the ability to make the antibodies for themselves. More specifically called passive antibody protection, this defense mechanism is passed to the young of mammals through the placenta, the mother's milk, or through both. The young of birds, however, receive their passive antibody protection through the store of antibodies placed in the eggs in which they develop from the embryonic stage. Birds, in particular, have the ability to "load up" their eggs as they are formed, with a very large supply of antibodies concentrated over that which is present in the serum of the mother. In addition, avian antibodies are much more stable and resistant to inactivation through digestion than mammalian antibodies, especially under adverse conditions. Once immunized, the hen layers the unique IgY types immunoglobulins in the yolk while depositing the common chicken IgM and IgA immunoglobulins in the albumin. The albumin helps add resistance to the whole egg preparations and helps protect the avian antibodies. The avian IgY immunoglobulins in the yolk tightly bind to, coat, cover and obliterate adherins which attach themselves to their hosts. The albumin, IgM and IgA immunoglobulins increase binding in the mucous tissue of the respiratory tract of the antibody containing material which provides longer sustaining effect of the antibody containing material. The IgM and IgA immunoglobulins have di-sulfide bonds that retain molecules together and provide larger antibody containing molecules. The larger antibody containing molecules are more effective in preventing adherence of the targeted immunogen in the respiratory tract of the animal or human. Albumin is a protein that protects the activity of the IgY immunoglobulins thereby increasing their active life in the respiratory tract. Furthermore, the large quantities of antibodies which are placed in eggs are much more exclusively those specific for the antigens to which the mother has most recently been exposed to and challenged by. This all results in the eggs of birds being a most idea source for large quantities of economically produced highly specific and stable antibodies. While the invention is illustrated by the use of chickens to produce avian antibody, other fowl including turkeys, ducks, geese, ostrich, Emu, pheasant, pigeon, quail, etc. or combination thereof, may be used.

Specifically, groups are obtained of young hen chickens, typically Rhode Island Reds, White Leghoms, sex-linked hybrid crosses or other breeds suited to large egg size, high volume egg production and ease of handling which are about to reach laying age, about 16-19 weeks for chickens, on a schedule predetermined by the amount and timing of final product desired resulting in a steady continuous production stream. After a suitable period of isolation and acclimatization of about two to four weeks, each group will enter into an inoculation program using rehydrated proprietary preparations of specific antigens (immunogens) to which an antibody is desired. The cultures of microorganisms may be obtained from commercial sources such as the American Type Culture Collection (ATCC). The cultures may be used to isolate antigens. The antigens can be prepared as prepared immunogens and may be injected intramuscularly, but preferably injected subcutaneously. In approximately four to five weeks, the average egg collected will contain copious amounts of the desired specific antibody in a readily usable and stable form. The chickens may be reinoculated with the targeted immunogen throughout the egg laying period to maintain the high antibody level.

Batches of eggs from predetermined groups of chickens are cracked, the contents are separated from the shells and mixed and preferable pasteurized to eliminate potential pathogenic microorganism from the chicken and thus reduce potential contamination. Standard test procedures are used, such as ELISA, agglutination, or the like are used to the monitor the antibody activity. The typical batch is then blended with batches from groups of chickens at other average production levels resulting in abundant standardized active ingredients. The egg antibody microbial inhibitor material may be stored and shipped on carrier materials such as soy bean oil, boluses and/or tablets. Dependent on the needs and specifications of the formulator and the final customer, the final antibody products may include some type of innocuous additive, such as dried whey or soy hulls, distillers grains, molasses, soy or rice husks or the like for formulation with feed ration. One egg produced and processed by the above procedures will yield a product sufficiently active and stable to provide at least as many as 140 to 160 doses of managed protection against specific microbial colonization. This method provides for the first time, an economical, safe and effective means for controlling respiratory illness causing organisms in beef cattle and dairy herds, swine, chickens, turkeys, companion animals, high value nonfood animals, zoological animals and humans.

Immunogen adherence inhibitor and method of making and using same produces specific immunogens to the microbial species listed. The immunogens are used to immunize egg laying avian animals. The immunized hen will lay eggs containing the specific antibodies of the IgM and IgA type in the albumen and IgY type in the yolk. The eggs will be collected and material from the whole cracked egg will be mixed in the proper concentration with a carrier mixture such as molasses, soy oil, DMSO, PBS buffer and Vitamin E solution. This solution is optimized so it can be sprayed, squirted, injected intra-nasally, gelled, or used on top feed and in lick tubs. The protective material may be sprayed over the animals in the pens or feedlots during the feeding period usually once in the morning and once in the evening. The number of sprayings is determined from testing. Since the material is non-toxic, it is given as needed and as much as needed for a given pen. The preferred method is by direct intra-nasal injection with a spray using ½ dose per nostril or a combination of direct nasal spray plus top feed, lick tub, squirt applicators.

The product is an all natural preparation that contains specific avian antibodies to the targeted immunogens. These antibodies when attached to the outer surface cell wall, adherin receptors, pilii or pilated structures and capsule, or viral capsid will not allow the organism to attach to the mucous membranes. The microorganisms will not be able to multiply or colonize. It will keep the microorganisms from moving down the respiratory tract and eliminates the ability to cause disease in the lower respiratory tract. By spraying the material, the mist will coat the nasopharynx and prevent the bacteria, viruses or other microorganisms from being spread in water droplets. The mist will also coat the feed and water in the area, again blocking the ability of the organisms to spread from animal to animal. The method of the invention provides for a substantial decrease in animal illness and death in feedlots and pens without the use of antibiotics.

By reducing respiratory organisms, one will decrease lung lesions, reduce secondary infection, improve daily gain, improve performance, improve feed efficiency, and reduce costs. Controlling pneumonia in animals will improve growth performance and quality of life as well as lower potential spread of respiratory organisms. Similar examples can be obtained in companion animals or humans. It is apparent that many modifications and variations of this invention as hereinbefore set forth may be made without departing from the spirit and scope thereof. The specific embodiments described are given by way of example only and the invention is limited only by the terms of the appended claims.

The most successful colonizing microorganisms, bacteria, viruses and parasites, etc., have evolved a number of different types of molecules, referred to as “adherins” or “intimins”, on their surfaces which can very tightly stick to one or more types of specific molecules that are part of the host’s various surfaces. The adhesion inhibitor is an avian antibody of extraordinary high specific activity which can very tightly bind to, coat, cover and obliterate these adherins which attach themselves to their hosts with a lock and key type of fit to very unique chemical structures. The avian IgY immunoglobulins in the yolk tightly bind to, coat, cover and obliterate adherins which attach themselves to their hosts. The albumin, IgM and IgA immunoglobulins increase binding in the mucous tissue of the respiratory tract of the antibody containing material which provides longer sustaining effect of the antibody containing material. The IgM and IgA immunoglobulins have di-sulfide bonds that retain molecules together and provide larger antibody containing molecules. The larger antibody containing molecules are more effective in preventing adherence of the targeted immunogen in the respiratory tract of the animal or human. Albumin is a protein that protects the activity of the IgY immunoglobulins thereby increasing their active life in the respiratory tract. In addition to this direct attack, components of the complement system included in most biological fluids, such as blood, lymph, saliva, tears and to some extent intestinal secretions, recognize an antibody attachment as triggers for their many types of defensive activities. Specific antibody attachment and coating combined with the very likely mobilization of many other cellular defense systems, therefore, quickly culminating in the chemical inactivation and ultimately the destruction of the targeted microorganism.

The invention is further illustrated by the following examples:

EXAMPLE 1

Selection of Egg Laying Avian Hens

The strain of egg laying hen may vary with needs and uses. Any egg laying fowl hens may be immunized including chickens, turkeys, ducks, goose, pigeon, quail, ostrich, emus or any other fowl. The common strains of egg laying chickens are the preferred and are usually selected for the number of eggs laid per year, size of egg and ease of housing. Rhode Island Red, White Leghorn, and Red Sex Linked hybrids are the animals of choice based on egg size (large to ex-large, 50-65 gm) and were used for the immunization schedules. The ease of handling the animals and the size and uniformity of the eggs along with the number of eggs laid per hen per year were observed. Although any avian egg laying hen could be used, for cost and ease of use these chickens proved to work the best. The White Leghorn, W98 Hybrid gave the most uniformity and greater number of eggs per animal. These animals produce a large to extra-large grade of egg (50-65 gm) and up to 300 eggs a year per hen.

EXAMPLE 2

Preparation of PM Antigen for Immunogen

*Pasteurella Multicoda* (ATCC 15743) was used as a model bacteria. The organism was isolated from cattle. The ATCC method for rehydration of the stock was followed. The bacteria are re-hydrated in 1.0 ml of TSB. Brain Heart Infusion (BHI, Acumedia) is used to stimulate the PM antigens on the bacterium. Stock TSB is inoculated into BHI Broth and incubated at 37.degree. C. for 18-24 hours. This stimulates somatic and attachment antigens development on the bacteria. Flasks containing BHI Broth are inoculated with the BHI Broth culture. While stirring slowly, flasks are incubated at 37.degree. C. Blood agar plates are streaked for isolation of colonies to confirm the morphology. Good growth is seen after 22 hours. Flasks are combined and the material is harvested using centrifugation and sterile saline (0.9%) at approximately 3000 rpm for 30 minutes. The harvest is collected in tubes. Density is checked using spectrophotometer enumeration and McFarland nephelometer standards. The material is diluted to approximately 1.times.10.sup.9 per ml. Four percent (4%) sodium deoxycholate (Difco) solution is added as a 1:1 ration with culture in 0.9% sterile saline (Herzberg, 1972) and stirred for approximately 18 hours at room temperature (22.degree. to 24.degree. C.). The material is centrifuged to remove whole cells. Supernatant is used as stock for PM antigen. Dry weight is determined at approximately 14.9 mg/ml. The product is diluted in sterile PBS, pH 7.4 to 1 mg/ml for PM Immunogen.

EXAMPLE 3

Preparation of PH Antigen for Immunogen

Use stock *P. Haemolytica* (ATCC 14000) as stock for PH antigen. The organism was isolated from cattle. The ATCC method for rehydration of the stock was followed. The bacteria are re-hydrated in 1.0 ml of TSB. Brain Heart Infusion (BHI, Acumedia) is used to stimulate the PM antigens on the bacterium. Stock TSB is inoculated into BHI Broth and incubated at 37.degree. C. for 18-24 hours. This stimulates somatic and attachment antigens development on the bacteria. Flasks containing BHI Broth are inoculated with the BHI Broth culture. While stirring slowly, flasks are incubated at 37.degree. C. Good growth is seen after 22 hours. Blood agar plates are streaked for isolation of colonies to confirm the morphology. Flasks are combined and the material is harvested using centrifugation and sterile saline (0.9%) at approximately 3000 rpm for 30 minutes. The harvest is collected in tubes. Density is checked using spectrophotometer enumeration and McFarland nephelometer standards. The material is diluted to approximately 1.times.10.sup.9 per ml. Four percent (4%) sodium deoxycholate (Difco) solution is added as a 1:1 ration with culture in 0.9% sterile saline (Herzberg, 1972) and stirred for approximately 18 hours at room temperature (22.degree. to 24.degree. C.). The material is centrifuged to remove whole cells. Supernatant is used as stock for PH antigen. Dry weight is determined. The product is diluted in sterile PBS, pH 7.4 to 1 mg/ml for PH Immunogen.

EXAMPLE 4

Preparation of HS Antigen for Immunogen

Stock *Haemophilus sommus* (ATCC 43626) can be used as stock bacterial culture for HS antigen. The organism was isolated from cattle. The ATCC method for rehydration of the stock was followed. The bacteria are re-hydrated in 1.0 ml of TSB. ATCC medium: 814 GC Medium is used to stimulate the HS antigens on the bacterium. Stock TSB is inoculated into 814 GC Medium and incubated at 37.degree. C. and 5% CO.sub.2 for 18-24 hours. This stimulates somatic and attachment antigens development on the bacteria. Good growth is seen after 22-48 hours. Blood agar plates are streaked for isolation of colonies to confirm the morphology. Flasks are combined and the material is harvested using centrifugation and sterile saline (0.9%) at approximately 3000 rpm for 30 minutes. The harvest is collected in tubes. Density is checked using spectrophotometer enumeration and McFarland nephelometer standards. The material is diluted to approximately 1.times.10.sup.9 per ml. Four percent (4%) sodium deoxycholate (Difco) solution is added as a 1:1 ration with culture in 0.9% sterile saline (Herzberg, 1972) and stirred for approximately 18 hours at room temperature (22.degree. to 24.degree. C.). The material is centrifuged to remove whole cells. Supernatant is used as stock for HS antigen. Dry weight is determined. The product is diluted in sterile PBS, pH 7.4 to 1 mg/ml for HS Immunogen.

EXAMPLE 5

Preparation of HSa Antigen for Immunogen

Use stock *Haemophilus suis* (ATCC 19417, *H. parasuis*) as stock for HSa antigen. The organism was isolated from swine. The ATCC method for rehydration of the stock was followed. The bacteria are re-hydrated in 1.0 ml of TSB. ATCC Medium 5129: Haemophilus Test Medium is used to stimulate the HSa antigens on the bacterium. Stock TSB is inoculated into #5129 Broth and incubated at 37.degree. C. for 24-48 hours. This stimulates somatic and attachment antigens development on the bacteria. Flasks containing #5129 Broth or plates containing #814 Medium are inoculated with Stock Broth culture. Flasks are incubated at 37.degree. C. and 5% CO.sub.2. Good growth is seen after 48 hours. Blood agar plates are streaked for isolation of colonies to confirm the morphology. Flasks are combined and the material is harvested using centrifugation and sterile saline (0.9%) at approximately 3000 rpm for 30 minutes. The harvest is collected in tubes. Density is checked using spectrophotometer enumeration and McFarland nephelometer standards. The material is diluted to approximately 1.times.10.sup.9 per ml. Four percent (4%) sodium deoxycholate (Difco) solution is added as a 1:1 ration with culture in 0.9% sterile saline (Herzberg, 1972) and stirred for approximately 18 hours at room temperature (22.degree. to 24.degree. C.). The material is centrifuged to remove whole cells. Supernatant is used as stock for HSa antigen. Dry weight is determined. The product is diluted in sterile PBS, pH 7.4 to 1 mg/ml for HSa Immunogen.

EXAMPLE 6

Preparation of ELISA Plates Using PH, PM, HS and HSa Antigens for Monitoring Antibodies in Eggs Chickens and Feed PH, PM, HS and HSa ELISA: Ninety-six well assay plate (flat bottom Costar) were coated using 100 .mu.l/ml with various concentration of antigens (10 .mu.g-200 .mu.g/ml) in carbonate buffer, ph 9.6. Plates were incubated between 22.degree. to 37.degree. C. for up to 18 hours. The wells were aspirated to prevent cross-contamination. The plates were blocked with 390 .mu.l/well of 0.5% BSA and incubated at 37.degree. C. for 1 hour. Plates were coated using alternative rows of positive or negative for controls. Plates were rinsed one time with wash buffer containing Tween™ 20. One hundred microliters per well of diluted sample are added to wells in duplicate wells, and incubated at 37.degree. C. for one hour. Goat anti-chicken IgG conjugate with Horseradish peroxidase (Kirkegard and Perry Laboratories; 1:1000 to 1:3000) was added. After one hour incubation, the substrate (TMB, KPL) was added according to manufacturer's instructions and the reaction is stopped after 10 minutes with 0.1 M phosphoric acid. Optical densities of the wells were determined in Dynatech ELISA Reader at 450 nm and the information was recorded for further data analysis.

EXAMPLE 7

Analysis of Individual Eggs and Serum Over Time

Eggs were selected at various periods in the immunization period for monitoring antibody responses to the specific antigens. Selected chickens were monitored at day 0 and continued on a monthly basis after the fourth month. The whole egg was collected from the shell and then a 1 ml sample was taken. This sample was then extracted with buffer to analyze the antibody content. The standard ELISA's for the PH, PM, HS and HSa immunogens were used for analysis. The negative readings were subtracted from the OD readings.

EXAMPLE 8

Immunization of Chicken with PH Immunogen

Selected egg laying hens, White Leghoms, approximately 19 weeks old were injected with the stock PH immunogen. Four injections (500 .mu.g, 100 .mu.g, 200 .mu.g, and 250 .mu.g) were given one week apart. A serum sample was collected two weeks after the last initial injection. If boosters were needed, 100 .mu.g was given in each booster (every six months). Within four weeks, all hens produced excellent antibodies in the eggs. EILSA PH readings averaged 1.00 OD for 1:10,000 dilution and 0.265 OD for 1:50,000.

EXAMPLE 9

Immunization of Chicken with PM Immunogen

Selected egg laying hens, White Leghoms, approximately 19 weeks old were injected with the stock PM Immunogen. Four injections (500 .mu.g, 100 .mu.g, 200 .mu.g and 250 .mu.g) were given one week apart. A serum sample was collected two weeks after the last initial injection. If boosters were needed, 100 .mu.g was given in each booster (every six months). Within four weeks, all of the hens produced excellent antibodies in the eggs. EILSA PM readings averaged 1.42 OD for 1:10,000 dilution an 0.68 OD for 1:50,000.

EXAMPLE 10

Immunization of Chicken with HS Immunogen

Selected egg laying hens, White Leghoms, approximately 19 weeks old were injected with the stock HS Immunogen. Four injections (500 .mu.g, 100 .mu.g, 200 .mu.g and 250 .mu.g) were given one week apart. A serum sample was collected two weeks after the last initial injection. If boosters were needed, 100 .mu.g was given in each booster (every six months). Within four weeks, all hens produced excellent antibodies in the eggs. EILSA HS readings averaged 0.95 OD for 1:10,000 dilution an 0.250 OD for 1:50,000.

EXAMPLE 11

Immunization of Chicken with HSa Immunogen

Selected egg laying hens, White Leghoms, approximately 19 weeks old were injected with the stock HS Immunogen. Four injections (500 .mu.g, 100 .mu.g, 200 .mu.g and 250 .mu.g) were given one week apart. A serum sample was collected two weeks after the last initial injection. If boosters were needed, 100 .mu.g was given in each booster (every six months). Within four weeks, all hens produced excellent antibodies in the eggs. EILSA HSa readings averaged 1.40 OD for 1:10,000 dilution an 0.576 OD for 1:50,000.

EXAMPLE 12

Preparation of Stock Production Whole Egg Reagents

Selected hens were combined from all four immunogen groups to be used to produce production batches of whole egg reagents. Sterling (U.S. Pat. No. 5,753,228) presents and excellent review of uses for the selection of eggs and storage of the same. The eggs were randomized and shell removed. The whole egg is mixed well and pasteurized using standard conditions (60.degree. C. (140.degree. F.) for 3.5 minutes) Charley, H. and C. Weaver, 3.sup.rd Edition, Foods: a scientific approach, Merril-Prentice Hall, p. 350, 1998). Once pasteurized, samples were tested for activity and store at 4.degree. C. until dried or sprayed onto carriers. Samples of 250 .mu.l were analyzed. Examples of results for ELISAs are given:

Pasteurized Whole Egg: PM, PH, HS, HSa Mixtures

1 Immunogen Dilution O.D PM 500 0.532 PM 2500 0.113 PH 500 0.466 PH 2500 0.115 HS 500 0.338 HS 2500 0.128 HSa 500 0.588 HSa 2500 0.155

EXAMPLE 13

Analysis of Feed Additives for Antibody Activity

Samples of the material were collected from three batches. The samples were analyzed using the ELISA systems for PH, PM, HS and HSa immunogens to monitor activity after pasteurizing and storage. Good antibody response was recorded after the processing of the whole egg batches. Data from three batches from example 20 method of production is given in the table below:

2 Pasteurella Haemophilus Batch: Liquid Immunogen Signal/Noise Immunogen Signal/Noise Batch #1 0.347 5.32 0.111 2.68 Batch #2 0.188 2.92 0.175 2.93 Batch #3 0.272 2.98 0.138 1.91

EXAMPLE 14

Testing on Feed Lot Cattle

A group of 222 calves from 2 different sources were shipped to Idaho. 109 calves were processed on day 0 and 113 processed on day 2. All calves received normal vaccination and processing which includes antibiotics designed to reduce disease stress and to increase average daily gain and feed efficiency. Half of the group received the material by intranasal administration. Doses were directly injected into the nostril (1.5 cc/nostril: total 3 ml). The animals were tagged and monitored for 35 days. All calves were housed in the same pen. The Test group had N=111 and the Control group had N=111. The following was observed:

3 Controls (n=111) Test (n=111) Number Percent Number Percent Pulled to 20 18 7 6 Hospital Treated for 19 17 7 6 Respiratory Disease Deaths 3 3 0 0 Died from 2 2 0 0 Respiratory Disease Retreats 5 3

EXAMPLE 15

Testing of Feed Lot Cattle

A group of 165 sale barn calves were shipped in the middle of summer. Calves were processed on day 0 and on day 2. All calves received normal vaccination and processing which includes antibiotics designed to reduce disease stress and to increase average daily gain and feed efficiency. Half of the group received the material by Intranasal administration. Doses were directly injected into the nostril (1.5 cc/nostril: total 3 ml). The animals were tagged and monitored for 35 days. Test group had N=82 and the Control group had N=83. The following was observed: Controls (n=83) Test (n=82)

4 Controls (n=83) Test (n=82) Number Percent Number Percent Pulled to 36 47 24 28 Hospital Treated for 36 43 22 25 Respiratory Disease Deaths 9 5 Died from 8 4 Respiratory Disease Retreat 1× 14 12 Treated 2× 10 4 Treated 3× 4 3 Treated 4× 3 2 Treated 5× 6 1 Treatment Cost $1,291.44 $ 796.51 Ave. Cost per $35.87 $ 30.64 Animal treated

EXAMPLE 16

Testing of Feed Lot Cattle

Two groups of calves were shipped to Idaho. 77 calves were processed on day 0 from the first group. Half of the groups were processed as Test (n=39) and other half as Control (n=38). The second group of 78 were processed the same on day 2. All calves received normal vaccination, wormer, implants, and processing which includes antibiotics designed to reduce disease stress and to increase average daily gain and feed efficiency. The Test group received the material by Intranasal administration. Doses were directly injected into the nostril (1.5 cc/nostril: total 3 ml). The animals were tagged and monitored for 35 days. The Test group animals that were pulled to the hospital received booster material along with normal treatment each time they went through the chute. The control cattle received only the normal treatment. The Test group had N=77 and the Control group had N=78. The following was observed:

5 Controls (n=78) Test (n=77) Number Percent Number Percent Pulled to 18 23 13 17 Hospital Treated for 18 23 13 17 Respiratory Disease Deaths 1 1 Died from 1 1 Respiratory Disease Retreat 1× 6 5 Treated 2× 7 5 Treated 3× 3 3 Treated 4× 2 0 RES Realizers 1 2 RES Deads 1 1 Death Rate 1.28 1.30 Treatment Cost $691.49 $478.59 Ave. Cost per $38.42 $ 36.81 Head Pulled Treatment $8.87 $6.22 Cost/Head in Pen

EXAMPLE 17

Testing of Weaned Calves

Four groups of calves were weaned at approximately 1000 to 2000 calves per week. The calves were processed as small groups. All calves received normal vaccination, wormer, implants, and processing which includes antibiotics designed to reduce disease stress and to increase average daily gain and feed efficiency. The groups all received the material by Intranasal administration. Doses were directly injected into the nostril (1.5 cc/nostril: total 3 ml). The animals were tagged and monitored for 22 days. The group animals that were pulled to the hospital received booster material along with normal treatment each time they went through the chute. Test group had N=5000. After 22 days only 50 animals had been pulled for respiratory problems.

EXAMPLE 18

Testing Lick Tubs

The manufacturing process for the lick tubs is very simple and straightforward. The manufacture of this example is done by adding prepared wet material and distillers condensed syrup to standard tubs to adjust the moisture content upward. We substituted dryer material and our liquid material to achieve the same moisture content as standard tubs that are currently being made to achieve a finished tub with similar properties.

The Total Batch Manufactured Lick Tub Example Includes the Following Ingredients:

6 Dried Distillers Grains with Solubles (DDGS) 1170 pounds Corn Gluten Meal 1365 pounds Wet Distillers Grains (wet coke) 465 pounds Vitamin and Mineral premix 750 pounds Magnesium Oxide 600 pounds Mixed Antibody 540 liters Food grade Molasses 10 gallons Mold Inhibitor 6 pounds The DDGS, corn gluten meal, wet cake, mold inhibitor, premix and magnesium oxide are placed in a 5-ton mixer truck and mixed for 5 minutes. Then the material and Molasses are added. This is mixed for 30 minutes. The resulting material weighs approximately 5,630 pounds. This mixture is unloaded through a side discharge chute into twenty-eight 200-pound plastic tubs and then compressed into a solid material. The tubs are then cured for 48 hours into a very hard, bark brown product with a somewhat yeasty, sweet odor.

In one trial, one tub was placed near the cattle in a pen of one hundred ninety-seven 600-pound steers. The cattle in the test feedlot were very interested in this material. They visit the tubs several times a day. Consumption was about 7.7 grams/head/day. It is anticipated that per head consumption would be somewhat higher if more tubs were placed in the pen.

EXAMPLE 19

Development of Top Dressing

One of the key preparations can be used for Top Dressing. Specific whole egg is collected from hens immunized with PH, PM, HS and HAs antigens in equal amounts for a total of 7-9 L. The whole egg material is added to 2 L of PBS, pH 7.4, 4.5 L of molasses, and 4 L of distilled water. This is mixed well and preservatives such as food grade vitamin E, vanilla, sodium benzoate, potassium sorbate and sodium citrate are added to prevent microbial growth and extend shelf-life. The total amount is 18 L. The mixture is stirred to get a homogenous solution. The mixture is then pasteurized in a Food Pasteurizer from The Schlueter Company. The material is cooled and stored at 4.degree. C. until used.

This material is poured on top of the feed as needed. It usually is distributed once every 7 days for a total of three applications.

EXAMPLE 20

Development of Material for Aerosol or Spray

One of the key preparations can be used for Aerosol or spray. Specific whole egg is collected from hens immunized with PH, PM, HS and HAs antigens in equal amounts for a total of 10 L. The whole egg material is added to 6 L of PBS, pH 7.4 and 2 L of molasses. This is mixed well and preservatives such as food grade vitamin E, vanilla, sodium benzoate, potassium sorbate and sodium citrate are added to prevent microbial growth and extend shelf-life. The total amount is 18 L. The mixture is stirred to get a homogenous solution. The mixture is then pasteurized. The material is cooled and stored at 4.degree. C. until used.

This material is sprayed directly over the heads of the animals to form an aerosol. The material can also be poured into pressure guns such as squirt guns. Cowboys can carry these loaded guns out on the range or in the feedlot pens and deliver directly to the cattle as needed. The material can be sprayed directly on the nose of the individual animals as needed. This makes for a very versatile means of application out on the range. It usually is distributed once every 7 days for a total of three applications or as needed.

EXAMPLE 21

Animal Testing of Swine

A group of 77 feeder pigs approximately 60 lbs each were tested with material made in Example 20 for Top Dressing. The animals were given the material as a top dressing on days 0, 7, 14 and 21. The average losses on this farm over the last 5 years, due to respiratory complex, was 7.5% and over 30% were medicated during the first 21 days of placement in pens. During the test period of 62 days, all animals were in excellent condition and ahead of schedule with 0% losses and 0% medicated.

EXAMPLE 22

Animal Testing of Swine

A group of 80 feeder pigs approximately 50 lbs and considered the runts of the groups were tested with material made in Example 20 for Top Dressing. The animals were given the material as a top dressing on days 0, 7, 14 and 21. The average losses on this farm due to respiratory complex were 5% during the first 21 days and over 30% were medicated. These were the animals that had not done well in the past. This was the average for the farm over the last 5 years. During the test period of 55 days, all animals were in very good condition and ahead of schedule and better than in the past with 1.25% losses and 0% medicated.

Any microorganism which colonizes the nasal pharyngeal region of the respiratory tract of its host must possess the capability of sticking or adhering to the surface of the mucus membranes in order to multiply. The respiratory pneumonia complex organisms such as *Pasteurella multocida, M. haemolytica, Haemophilus somnus*, Swine influenza viruses and *Mycoplasma* bacteria are no exception to the rule. Other microorganisms from the fungi and parasite groups are included in organisms that may cause respiratory problems in animals or humans. The adherence inhibitor of this invention strongly interferes with adherence and on a cumulative basis, thereby prevents the specific targeted microorganism from colonizing, and multiplying and moving down the respiratory tract and infecting the lower tract including the lungs. Through the vehicle of a simple nasal injection, spray, by top feed or lick tub, the product essentially supplies the host with specific antibody preparation designed not to cure any disease in the animal but merely to dislodge any resident microorganism and to prevent the attachment of any newly introduced microorganism in the upper respiratory tract. The adherence inhibitor has no direct effect on the host itself, is all natural, leaves absolutely no undesirable residue in the animals, and thus has no effect whatsoever on the ultimate food products. In addition, since the microorganism is prevented from multiplying, it will over time (for example 21-30 days) disappear through natural degradation from mucus of the animal, eliminating the significant potential source of contamination in the feedlot. Properly managed, the risk of cross contaminating other animals throughout the feedlot is lowered and essentially eliminated. Similar applications could be developed for companion animals, zoological animals or nonfood animals or humans. They too have respiratory problems.

It is apparent that many modifications and variations of this invention as hereinbefore set forth may be made without departing from the spirit and scope thereof. The specific embodiments described are given by way of example only and the invention is limited only by the terms of the appended claims. The embodiments of the invention in which an exclusive property or privilege is claimed as follows.

The invention claimed is:

1. An intranasal composition comprising an egg mixture for administration to animals, the egg mixture comprising whole egg contents, food grade Vitamin E and one or more preservatives and/or carrier, wherein the whole egg contents are separated from the egg shells and are from eggs laid by female birds inoculated with an organism mixture comprising one or more microbial organisms causing respiratory illnesses, wherein the whole egg contents comprise adherence inhibiting material against the one or more microbial organisms that inhibits the ability of the one or more microbial organisms to adhere to the mucus membranes and bronchi and alveolar cells and multiply in the respiratory tract of the animals, wherein the composition is formulated for nasal administration, wherein the carrier and/or a preservative is selected from PBS buffer, molasses, soy oil, DMSO, vanilla, potassium sorbate, sodium citrate and combinations thereof.

2. The composition of claim 1, wherein the composition further comprises water.

3. The composition of claim 1, wherein the composition further comprises carrier material selected from soybean oil, distilled dried grains, beet pulp and/or combinations thereof.

4. The composition of claim 1, wherein the one or more organisms are bacteria, viruses, fungi or parasites.

5. The composition of claim 1, wherein the one or more organisms that the female birds are inoculated with are selected from *Pasteurella Haemolytica, Pasteurella Multicoda, Haemophilus somnus, Haemophilus parasus* and *Haemophilus suis* and combinations thereof.

6. The composition of claim 1, wherein the one or more organisms is selected from swine influenza virus, $H_1N_1$, $H_5N_1$, $H_3N_2$, Infectious Bovine Rhinotracheitis, 1 and 5, BRSV and $PI_3$, porcine respiratory and reproductive syndrome virus (PRRSv), Bovine adenovirus 1, 3, 5, 6, 7 and combinations thereof.

7. The composition of claim 1, wherein the composition comprises microbial adherence inhibitor against two to five microbial organisms.

8. The composition of claim 1, wherein the egg contents are from eggs laid by female birds inoculated with one microbial organism.

9. The composition of claim 1, wherein the egg contents are from eggs laid by female birds inoculated with multiple microbial organisms.

10. The composition of claim 1, wherein the egg contents are from eggs laid be female birds inoculated with the same organism or organisms.

11. The composition of claim 1, wherein the egg contents are from eggs laid be female birds inoculated with different organism or organisms.

12. The composition of claim 1, wherein the animals are selected from bovine, swine, poultry, zoological animals, companion animals or other farm animals.

13. The composition of claim 1, wherein the animals are humans.

14. The composition of claim 1, wherein at least about 35% of the composition is the whole egg contents.

15. The composition of claim 1, wherein the whole egg contents are less than about 60% of the composition.

* * * * *

UNITED STATES PATENT AND TRADEMARK OFFICE

CERTIFICATE OF CORRECTION

PATENT NO. : 10,407,494 B2
APPLICATION NO. : 15/645693
DATED : September 10, 2019
INVENTOR(S) : Bradley M. Mitteness It is certified that error appears in the above-identified patent and that said Letters Patent is hereby corrected as shown below:

On the Title Page

Item (56) In the Referenced Cited, on page 2, under Other Publications:
Please delete "Snowder et al., Bovine respiratory disease in feedlot cattle: environmental, genetic and economic factors, American Socity of Animal Science, Vo. 84, pp. 1999-2008, 2006."
And insert --Snowder et al., Bovine respiratory disease in feedlot cattle: environmental, genetic and economic factors, American Society of Animal Science, Vo. 84, pp. 1999-2008, 2006.--

In the Claims

Column 16, Claim 10, Line 26:
Please delete "are from eggs laid be female birds inoculated with the same"
And insert --are from eggs laid by female birds inoculated with the same--

Column 16, Claim 11, Line 29:
Please delete "are from eggs laid be female birds inoculated with different"
And insert --are from eggs laid by female birds inoculated with different--

Signed and Sealed this
Fifth Day of May, 2020

Andrei Iancu
*Director of the United States Patent and Trademark Office*